US011684545B2

(12) United States Patent
Chang et al.

(10) Patent No.: US 11,684,545 B2
(45) Date of Patent: Jun. 27, 2023

(54) HEARING TRAINING DEVICE

(71) Applicants: Eyes'on Technology Co., Ltd., Taichung (TW); Asia University, Taichung (TW)

(72) Inventors: Hui-Shan Chang, Taichung (TW); Shin-Da Lee, Taichung (TW); Chen-Chao Hsu, Taichung (TW); Yao-Yu Liao, Taichung (TW)

(73) Assignees: EYES'ON TECHNOLOGY CO., LTD., Taichung (TW); ASIA UNIVERSITY, Taichung (TW)

( * ) Notice: Subject to any disclaimer, the term of this patent is extended or adjusted under 35 U.S.C. 154(b) by 523 days.

(21) Appl. No.: 16/887,864

(22) Filed: May 29, 2020

(65) Prior Publication Data
US 2020/0382884 A1    Dec. 3, 2020

(30) Foreign Application Priority Data

May 31, 2019   (TW) .................................. 108119052

(51) Int. Cl.
*A61H 39/00* (2006.01)
*A61N 5/06* (2006.01)
*H04R 25/00* (2006.01)

(52) U.S. Cl.
CPC .......... *A61H 39/00* (2013.01); *A61H 39/002* (2013.01); *A61N 5/0613* (2013.01); *A61N 5/0619* (2013.01); *A61H 2205/02* (2013.01); *H04R 25/70* (2013.01)

(58) Field of Classification Search
CPC ...... A61H 39/00; A61H 39/002; A61H 39/04; A61H 2205/02; A61H 2201/10;
(Continued)

(56) References Cited

U.S. PATENT DOCUMENTS

| 2005/0222608 | A1* | 10/2005 | Hou ...................... A61H 39/04 606/204 |
| 2013/0204315 | A1* | 8/2013 | Wongsarnpigoon ........................ A61N 1/0484 607/45 |
| 2015/0257683 | A1* | 9/2015 | Ashmore ............. A61B 5/0022 600/559 |
| 2017/0189267 | A1* | 7/2017 | Tsang ..................... A61H 39/08 |
| 2018/0132027 | A1* | 5/2018 | Hawkes ................. A61B 5/123 |

(Continued)

FOREIGN PATENT DOCUMENTS

CN    108721787 A   * 11/2018

OTHER PUBLICATIONS

Acupuncture Effective for Treating Hearing Loss, Apr. 9, 2015, Healthcare Medicine Institute, Acupuncture Continuing Education (Year: 2015).*

(Continued)

*Primary Examiner* — Catherine M Voorhees
(74) *Attorney, Agent, or Firm* — Muncy, Geissler, Olds & Lowe, P.C.

(57) ABSTRACT

A hearing training device, is provided, including: a wearable device configured for being worn on the head of a user; a playing device arranged on the wearable device; an acupoint stimulation device, served as a physiotherapy device, comprising a plurality of acupoint stimulation mediums arranged on the wearable device, respectively configured for stimulating a plurality of acupoints on the head of the user and related to hearing, and arranged at the positions of the wearable device corresponding to the acupoints respectively; and a control device being in signal connection with the playing device and storing at least one music file, wherein the control device controls the playing device to play the music file, a beat is formed in an audio track of the music file, and the beat decreases with time, and is fixed until the beat is between 10 Hz and 15 Hz.

11 Claims, 15 Drawing Sheets
(4 of 15 Drawing Sheet(s) Filed in Color)

(58) Field of Classification Search
CPC ...... A61H 2201/1604; A61H 2201/165; A61H 2201/5005; A61H 2201/5007; A61H 2201/501; A61H 2201/5048; A61H 2205/021; A61H 2039/005; A61H 2205/027; A61N 5/0613; A61N 5/0619; A61N 1/36036; A61N 1/0456; A61N 1/0484; A61N 1/3603; H04R 25/70; H04R 25/75; A61M 21/00; A61M 2021/0022; A61M 2021/0027; A61M 2021/0055; A61M 2021/0072; A61M 2205/8206; A61M 2209/088; A61M 2210/06; A61M 2210/0662; A61M 2210/0687

See application file for complete search history.

(56) References Cited

U.S. PATENT DOCUMENTS

| | | | | |
|---|---|---|---|---|
| 2018/0133507 | A1* | 5/2018 | Malchano | A61B 5/0036 |
| 2019/0336765 | A1* | 11/2019 | Charlesworth | A61N 1/0456 |
| 2020/0069966 | A1* | 3/2020 | Porter | G02B 27/0172 |
| 2020/0280801 | A1* | 9/2020 | Andersen | H04R 1/1075 |
| 2020/0306536 | A1* | 10/2020 | Wang | A61F 7/007 |
| 2021/0113835 | A1* | 4/2021 | Wingeier | A61B 5/4836 |

OTHER PUBLICATIONS

Jiaosun TE20: Nomenclature, Location, Functions, Indications, Dr. Ishwar Gyawali, Sep. 26, 2018, Acupuncture Nepal (Year: 2018).*
English translation of CN 108721787 (Year: 2018).*

* cited by examiner

HEARING TRAINING DEVICE

BACKGROUND OF THE INVENTION

Field of the Invention

The invention relates to a training device, in particular to a hearing training device.

Description of the Prior Art

In view of hearing loss and tinnitus, there are many different ways to treat or assist the hearing loss, such as medication, cognitive behavior therapy, hearing aids, noise reduction and masking equipment, etc. However, there are still many patients who complain that these treatments and rehabilitation have poor effects. In addition, a pathway for human to hear a sound includes receiving sound waves by an ear structure, signal transmission via auditory nerve and information processing of brain auditory cortex. However, existing treatments or hearing aiding methods are less specific to the brain and nerves for regulation.

The present invention is, therefore, arisen to obviate or at least mitigate the above-mentioned disadvantages.

SUMMARY OF THE INVENTION

Accordingly, it is an object of the present invention to provide a hearing training device capable of adjusting a brain auditory cortex.

Therefore, the hearing training device comprises a wearable device, a playing device, an acupoint stimulation device and a control device; the wearable device is configured for being worn on the head of a user; the playing device is arranged on the wearable device; the acupoint stimulation device, served as a physiotherapy device, comprises a plurality of acupoint stimulation mediums arranged on the wearable device, wherein the acupoint stimulation mediums are respectively configured for stimulating a plurality of acupoints on the head of the user and related to hearing, and the acupoint stimulation mediums are arranged at the positions of the wearable device corresponding to the acupoints respectively; and the control device is in signal connection with the playing device and stores at least one music file, wherein the control device controls the playing device to play the music file, a beat is formed in an audio track of the music file, the beat decreases with time, and the beat is fixed after the beat is between 10 Hz and 15 Hz.

The efficacy of the invention is as follows. By means of the music files, a new hearing training mode different from that in the past can be provided, the brain auditory cortex of a user can be invigorated; and the acupoint stimulation mediums and the playing device can be simultaneously worn and positioned on the head via the wearable device by the user, so that diversified auxiliary training effects can be achieved, and the use time can be shortened.

The present invention will become more obvious from the following description when taken in connection with the accompanying drawings, which show, for purpose of illustrations only, the preferred embodiment(s) in accordance with the present invention.

BRIEF DESCRIPTION OF THE DRAWINGS

The patent or application file contains at least one drawing executed in color. Copies of this patent or patent application publication with color drawings will be provided by the Office upon request and payment of the necessary fee.

Other features and effects of the invention will be apparent from the implementation with reference to the drawings, in which.

DETAILED DESCRIPTION OF THE PREFERRED EMBODIMENTS

Figure 1:
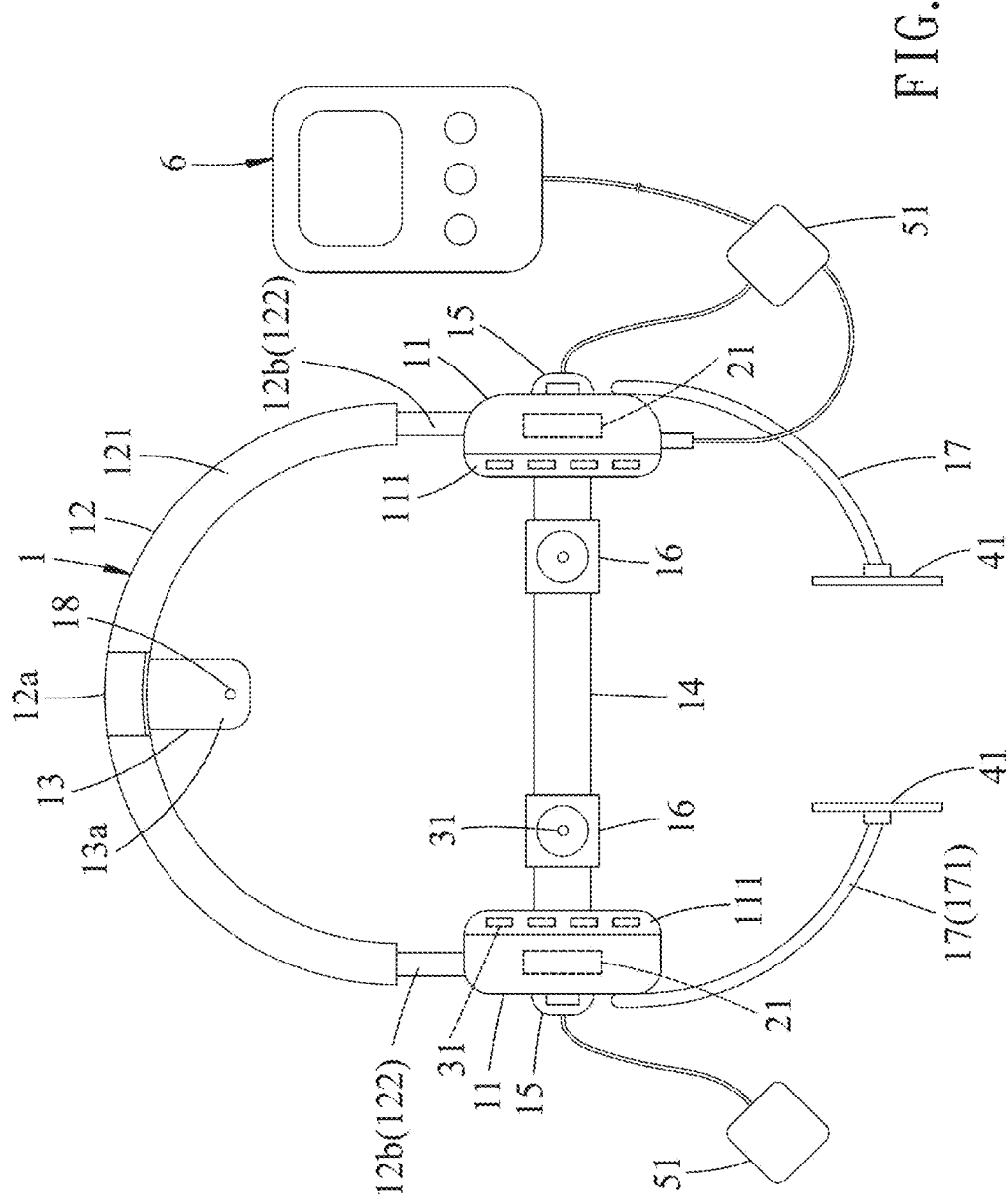
FIG. 1 is a schematically front view of a first embodiment of a hearing training device of the present invention.

Before the present invention is described in detail, it should be noted that like components are denoted by the same reference numerals in the following description.

Figure 2:
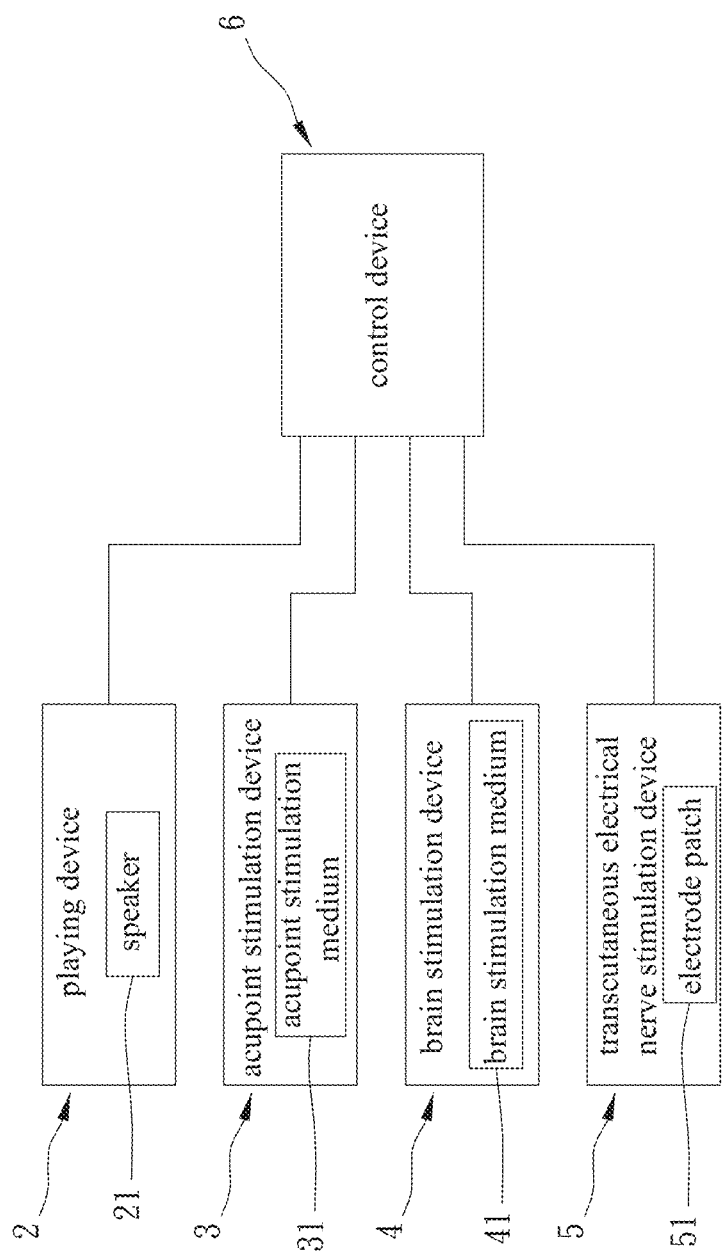
FIG. 2 is a functional block diagram of the first embodiment.

Referring to FIGS. 1 and 2, a first embodiment of a hearing training device of the present invention comprises a wearable device 1, a playing device 2, an acupoint stimulation device 3, a brain stimulation device 4, a transcutaneous electrical nerve stimulation device 5, and a control device 6.

With reference to the figures, the wearable device 1 is configured for being worn on the head of a user. The wearing device 1 comprises two earmuffs 11 configured for respectively covering both ears of the user, a first bracket 12 connected to the earmuffs 11 and configured for straddling over the top of the head of the user, a second bracket 13 connected to the central portion 12a of the first bracket 12 and extending in a forward bending manner, a third bracket 14 which is arc-shaped and configured for straddling over the hindbrain of the user, two pivoting parts 15 connected to the earmuffs 11 and the third bracket 14, two moving parts 16 arranged on the third bracket 14 and spaced along an extending direction of the third bracket 14, two bent pipes 17 which are respectively connected with the earmuffs 11 and can be flexible and positioned, and three positioning marks 18 (see FIGS. 1 and 5). Each earmuff 11 has a cushion 111 for abutting against the circumference of the user's ears. Each bent pipe 17 is provided with a power supply line therethrough and is made of the material of microphone of a conventional earmuff-type earphone and has a moving end 171 far away from the earmuff 11, the moving end 171 being movable and positionable with respect to the respective earmuff 11.

Figure 3:
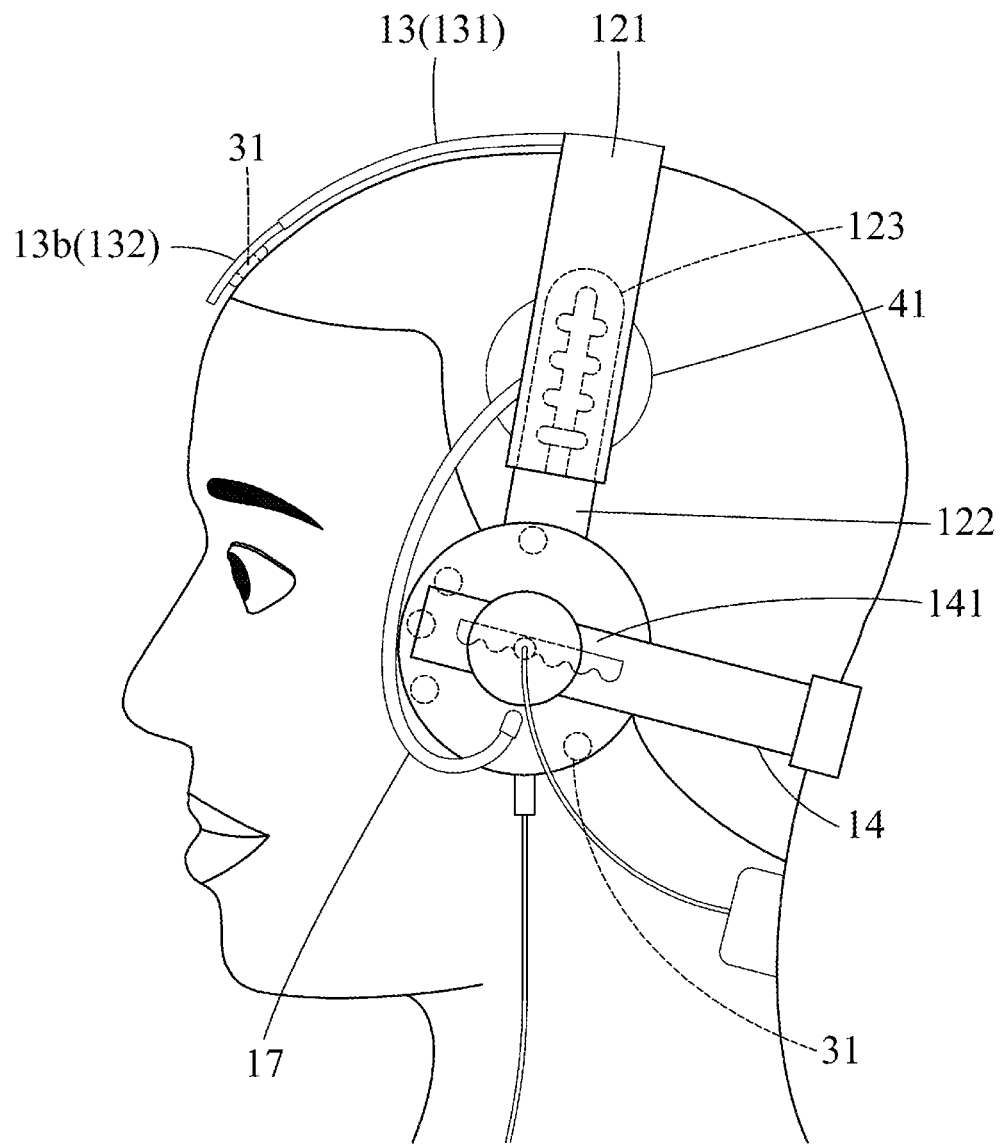
FIG. 3 is a fragmentary side view of the first embodiment illustrating a state in which the first embodiment is worn on the head of a user.

Referring to FIGS. 1 and 3, the first bracket 12 has an arc shape and also has two connecting portions 12b respectively connected to the earmuff 11, the central portion 12a is configured for corresponding to Baihui of the user, and the connecting portions 12b can be approached upward, moved downwardly and away, and positioned relative to the central portion 12a. In this embodiment, the first bracket 12 has a main sleeve 121, two auxiliary sleeves 122 slidably penetrating through both ends of the main sleeve 121 and connecting the earmuffs 11, and two first latch groups 123 disposed between the main sleeve 121 and the auxiliary sleeves 122, respectively; wherein the central portion 12a is positioned at the main sleeve 121, the connecting portions 12b are respectively positioned at the bottom ends of the auxiliary sleeves 122, the main sleeve 121 and the auxiliary sleeves 122 can be provided with power supply lines therethrough; the first latch group 123 can be configured for positioning the auxiliary sleeves 122 relative to the main sleeve 121, and the first latch group 123 adopts the existing structure of a latch group of earmuff-type earphones with adjustable length function; and since the structure of the first latch group 123 is conventional, it will not be described in detail herein.

The second bracket 13 has a front end positioned in front of the first bracket 12, the front end being approached backwards, moved forwards and away, and positioned relative to the central portion 12a of the first bracket 12. In this embodiment, the second bracket 13 has a fixed sleeve 131 connected to and communicating with the main sleeve 121, a moving sleeve 132 slidably penetrating the front side of the fixed sleeve 131, and a second latch group (not shown) disposed between the fixed sleeve 131 and the moving sleeve 132 and configured for positioning the moving sleeve 132; the front end 13a is positioned at the moving sleeve 132, and the fixed sleeve 131 and the moving sleeve 132 can be provided with power supply lines therethrough; as the structure of the second latch group is similar to that of the first latch group 123, it will not be described in detail.

Figure 4:
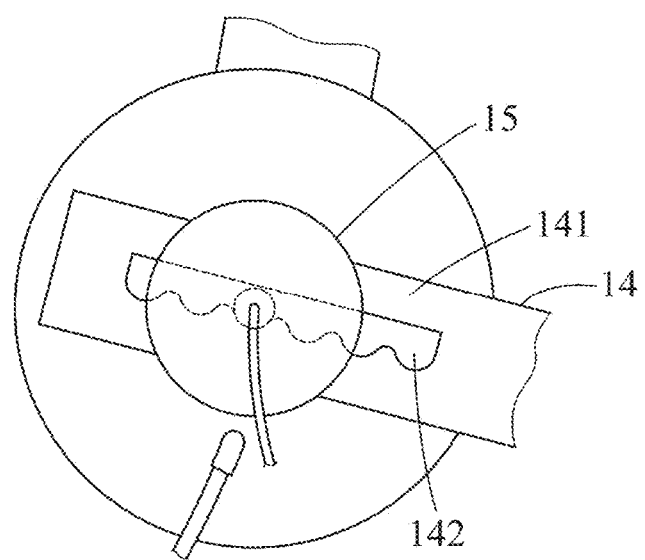
FIG. 4 is a fragmentary side view of a wearable device of the first embodiment illustrating a connection mode of one of earmuffs and a third bracket of the wearable device.

Referring to FIGS. 1, 3 and 4, the third bracket 14 includes two pivoting portions 141 pivotally connected to the earmuffs 11 respectively by the pivoting parts 15, and the third bracket 14 can swing up and down relative to the earmuffs 11. In this embodiment, each pivoting portion 141 of the third bracket 14 has an elongated slot 142 extending along the length direction thereof, the lower side of the elongated slot 142 is wavy, and each pivoting part 15 is inserted into a position where the width of the respective elongated slot 142 is large, and is screwed to the respective earmuff 11. Each pivoting portion 141 of the third bracket 14 is rotatable about a respective pivoting part 15, and can be pushed against the respective pivoting part 15 by an external force and deformed to slide relative to the respective pivoting part 15, so that the pivoting portions 141 can be moved and positioned along the length direction thereof relative to the pivoting parts 15 by the elongated slots 142. Furthermore, by screwing the pivoting parts 15 in the direction of the earmuffs 11, the third bracket 14 can be forced and fixed so that the third bracket 14 is positioned with respect to the earmuffs 11 and the first bracket 12.

Figure 5:
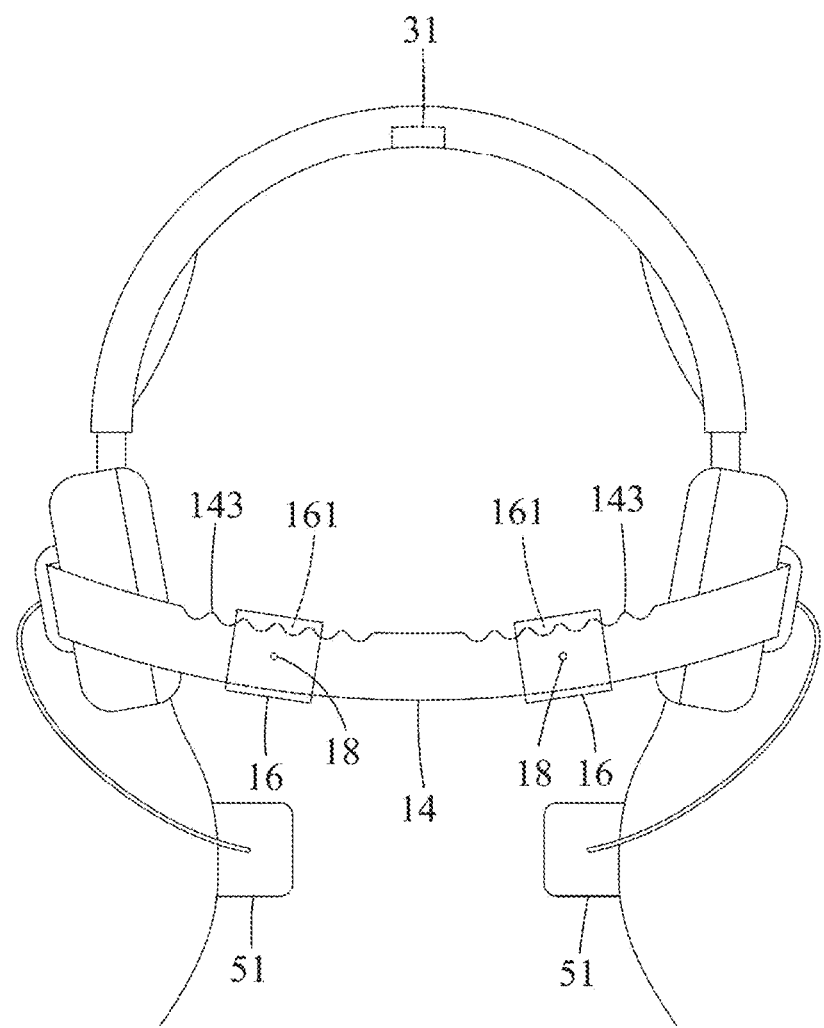
FIG. 5 is a schematically rear side view of the first embodiment illustrating a state in which the first embodiment is worn on the head of a user.

Referring to FIGS. 1 and 5, the moving parts 16 can move left and right and be positioned relative to the third bracket 14. In this embodiment, each moving part 16 is movably sleeved on the third bracket 14, and each moving part 16 has a wavy abutting portion 161 abutting against the third bracket 14. The third bracket 14 is also provided with two wavy positioning portions 143 corresponding to the abutting portion 161 of the moving parts 16, the abutting portions 161 are engaged with the positioning portions 143 to achieve the positioning effect, and the moving parts 16 can slide relative to the abutting portions 143 by an external force to move to the next engaging position.

The positioning marks 18 are disposed outside the front end 13a of the second bracket 13 and outside the moving parts 16, respectively, so as to be viewed from the outside.

Referring to FIGS. 1 and 2, the playing device 2 is provided on the wearable device 1 in the form of a conventional noise-reducing earphone and includes two speakers 21 respectively provided on the earmuffs 11.

Figure 6:
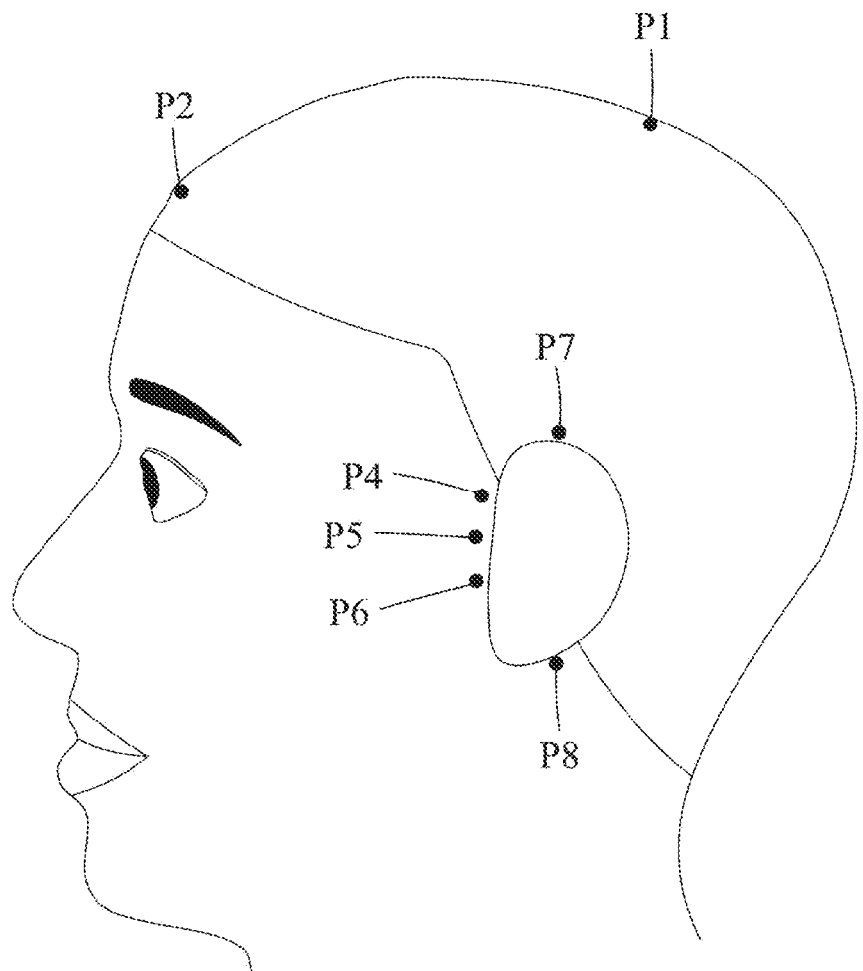
FIG. 6 is a schematic view of an acupoint of a plurality of acupoints corresponding to an acupoint stimulation device of the first embodiment.
Figure 7:
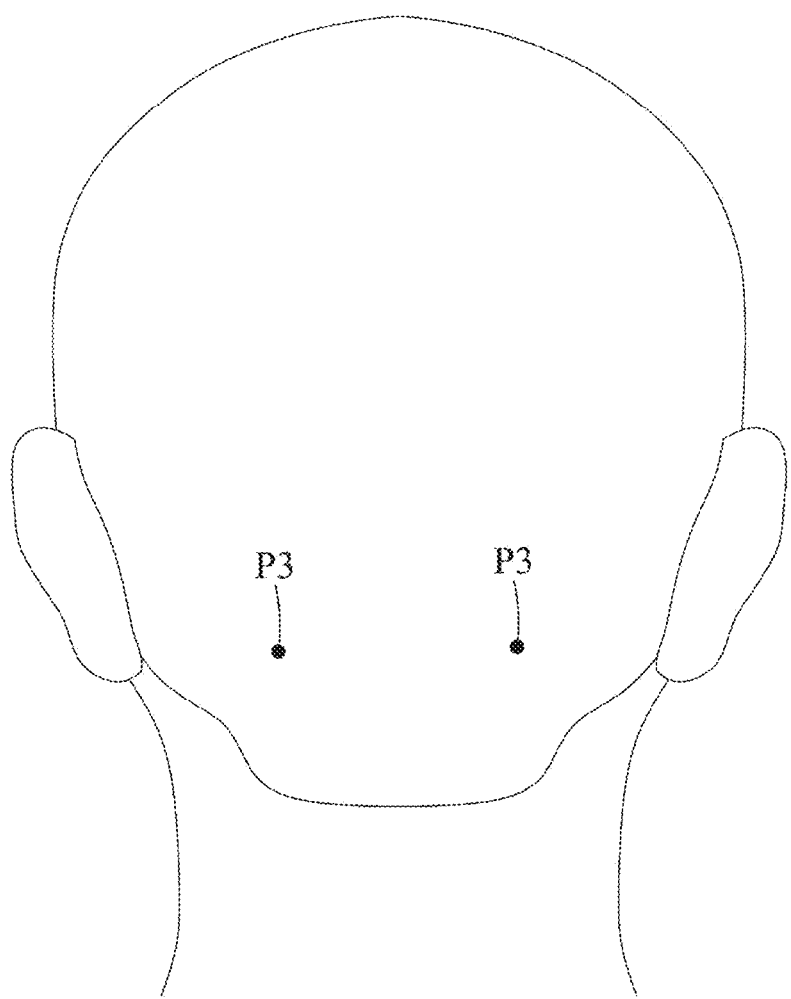
FIG. 7 is a schematic view of acupoints from another perspective of the plurality of acupoints corresponding to the acupoint stimulation device of the first embodiment.

Referring to FIGS. 1 to 3 and 5, the acupoint stimulation device 3 is a physiotherapy device, and the acupoint stimulation device 3 includes a plurality of acupoint stimulation mediums 31 disposed on the wearable device 1. The acupoint stimulation mediums 31 are respectively configured for stimulating acupoints P1-P8 (see FIGS. 6 and 7) on the head of a user and related to hearing, and the acupoint stimulation mediums 31 are arranged at the positions of the wearable device 1 corresponding to the acupoints P1-P8 respectively, so that the acupoints P1-P8 can be stimulated simultaneously. In this embodiment, there are fourteen acupoint stimulation mediums 31, one of which is provided at the central portion 12a of the first bracket 12, one of which is provided at the front end 13a of the second bracket 13 opposite to the corresponding positioning mark 18, and two of which are respectively provided at the moving parts 16 so as to be indirectly provided at the third bracket 14 opposite to the corresponding positioning mark 18. The other ten are arranged on cushions 111 of the earmuffs 11, and the acupoints P1-P8 corresponding to the acupoint stimulation mediums 31 are Baihui (see P1 of FIG. 6), Shenting (see P2 of FIG. 6), Fengchi (see P3 of FIG. 7), Ermen (see P4 of FIG. 6), Tinggong (see P5 of FIG. 6), Tinghui (see P6 of FIG. 6), Jiaosun (see P7 of FIG. 6) and Yifeng (see P8 of FIG. 6), respectively, wherein the acupoints P1-P8 correspond to hearing function. However, in other embodiments (on page 8, 17 in total, the description of the invention), the number of the acupoint stimulation mediums 31 and the corresponding acupoints P1-P8 are not limited thereto.

In this embodiment, the acupoint stimulation device 3 is a laser device, the acupoint stimulation mediums 31 are laser light generators, such as laser diodes, and are configured for irradiating laser light to the acupoints P1-P8; but in other embodiments, the acupoint stimulation device 3 may also be a magnet device, and the acupoint stimulation mediums 31 are magnets. In detail, since the acupoint stimulation mediums 31 arranged on the second bracket 13 and the moving parts 16 correspond to the positioning marks 18, the positioning marks 18 allow the user to distinguish the positions of three acupoint stimulation mediums 31 from the outside.

Figure 14:
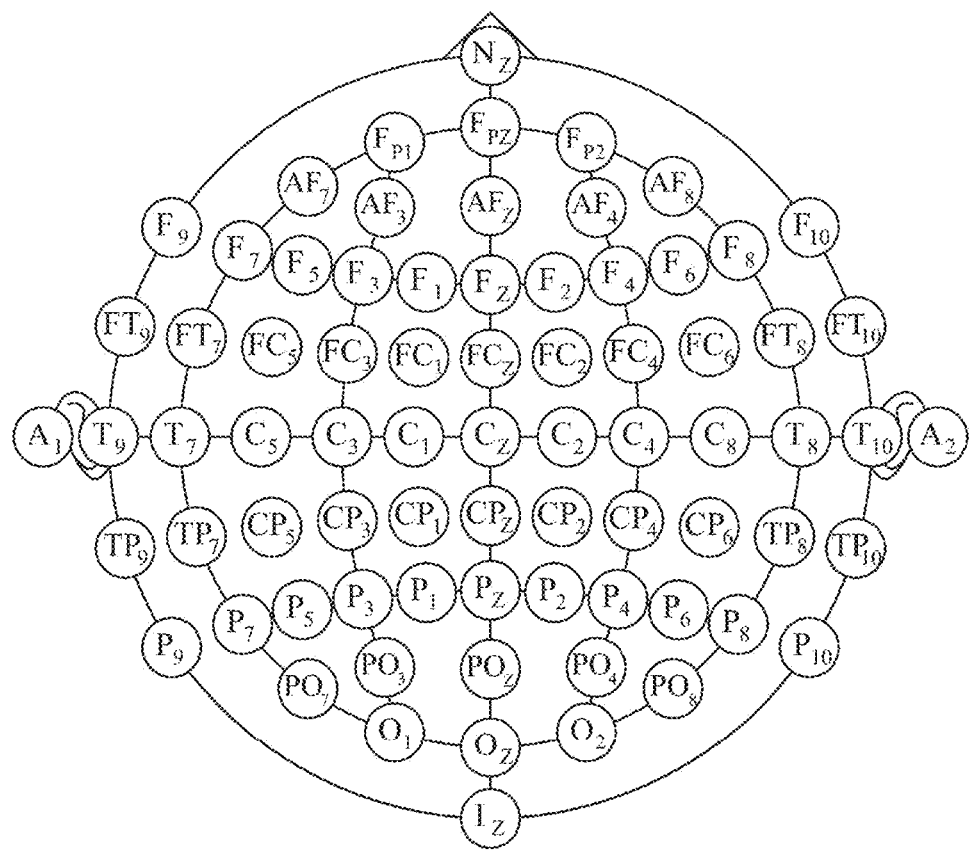
FIG. 14 is a schematic diagram of a location of an international 10-20 system scalp electrode.

Referring to FIGS. 1, 2 and 3, the brain stimulation device 4 is a physiotherapy device and includes at least one brain stimulation medium 41 arranged on the wearable device 1 for stimulating a brain cortex associated with hearing function of the user. In this embodiment, the brain stimulation device 4 is a transcranial direct current stimulation device and comprises two brain stimulation mediums 41 respectively arranged at the moving ends 171 of the bent pipes 17, wherein the brain stimulation mediums 41 are respectively an anode electrode and a cathode electrode and are configured for outputting direct current between 0 and 2.5 mA, and the bent pipes 17 are bent so that the brain stimulation medium 41, which is the anode electrode, is movable and positioned between C3 and T5 in the position of an international 10-20 system scalp electrode of the user's head (see FIG. 14), while the brain stimulation medium 41, which is the cathode electrode, is movable and positioned between T4 and F8.

Referring to FIGS. 1, 2 and 5, the transcutaneous electrical nerve stimulation device 5 can perform transcutaneous electrical nerve stimulation, and comprises two electrode patches 51 connected to the wearable device 1 and configured for being attached to the C2 nerve dermatome at the head and neck of the user; in this embodiment, the electrode patches 51 are configured to output a constant current having a pulse frequency of 1-200 Hz and an intensity of 0-100 mA.

Referring to FIGS. 1 and 2, the control device 6 is in signal connection with the playing device 2, the acupoint stimulation device 3, the brain stimulation device 4, and the transcutaneous electrical nerve stimulation device 5, and is operable by a user to control the operation of the playing device 2, the acupoint stimulation device 3, the brain stimulation device 4, and the transcutaneous electrical nerve stimulation device 5. The control device 6 stores a plurality of music files, the control device 6 controls the playing device 2 to play the music files with a sound intensity of 20-60 decibels, the sound intensity can be adjusted between 20-60 decibels during playing, and the control device 6 can also only store one music file.

The track of each music file is provided with a first audio frequency and a second audio frequency; the first audio frequency is between 250 and 8000 Hz, the first audio frequency and the second audio frequency form a beat; and the beat decreases with time, and is fixed after the beat is between 10 and 15 Hz. In the present embodiment, the music file mixes the first audio and the second audio in a track of an original music and converts it into an MP3 format for storage, with a bit rate of 128 Kbps and a sampling rate of 44.1 kHz; the first audio and the second audio are respectively introduced into tracks of different sound channels, so that the beat is a binaural beat; and the first audio and the second audio are respectively played by the speakers 21. In other embodiments, the first audio and the second audio may also be introduced into a track of the same sound channel, so that the beat is a monaural beat, and the first audio and the second audio may be played together by one of the speakers 21 or together by each of the speakers 21.

Further, in this embodiment, when each music file is synthesized, the first audio frequency is a frequency of a carrier wave, the second audio frequency is a frequency of a modulated wave, and the carrier wave and the modulated wave are sine waves; the first audio frequency does not change with time, the second audio frequency approaches the first audio frequency with time, the ranges of the first audio frequencies of the music files are different, and the first audio frequencies of the music files range from 250-500±15 Hz, 500-750±15 Hz, 750-1000±15 Hz, 1000-1500±15 Hz, 1500-2000±15 Hz, 2000-3000±15 Hz, 3000-4000±15 Hz, 4000-6000±15 Hz, 6000-8000±15 Hz respectively for a user to select a music file corresponding to his own hearing loss frequency for playing. For example, in one of the music files, the first audio frequency is 400 Hz, and the second audio frequency changes from 300 Hz to 388 Hz with time, so that the beat formed by the first audio frequency and the second audio frequency changes from 100 Hz to 12 Hz with time, and the beat can be selected and played by a user with the frequency of hearing loss containing 400 Hz.

In this embodiment, the control device 6 is electrically connected to the playing device 2, the acupoint stimulation device 3, the brain stimulation device 4 and the transcutaneous electrical nerve stimulation device 5, and control components (not shown) for controlling the operation of the acupoint stimulation mediums 31, the brain stimulation mediums 41 and the electrode patches 51 are provided in the control device 6. The control device 6 may be connected to a mains supply or powered by a battery, but in other embodiments, the control device 6 also can be connected to the playing device 2, the acupoint stimulation device 3, the brain stimulation device 4 and the transcutaneous electrical nerve stimulation device 5 wirelessly, and control components for controlling the operation of the acupoint stimulation mediums 31, the brain stimulation mediums 41 and the electrode patches 51 are arranged on the wearable device 1; and the wearable device 1 can be connected with a mains supply or provided with a battery for supplying power to the acupoint stimulation mediums 31, the brain stimulation mediums 41, the electrode patches 51 and control components thereof.

Referring to FIGS. 3 and 5, in use, a user first wears the wearable device 1 on the head, and then adjusts the wearable device 1 so that the acupoint stimulation mediums 31 are located at the acupoints P1-P8 of the user. In the adjusting process, the first bracket 12 can be adjusted so that the earmuffs 11 completely cover both ears, and the central portion 12a is positioned at an intersection where tips of the ears extend upwards, that is, the Baihui of the user, and then the positions of the second bracket 13, the third bracket 14 and the moving parts 16 are adjusted, so that the acupoint stimulation mediums 31 positioned on the second bracket 13 and the moving parts 16 are located at the Shenting and the Fengchi at both sides of the user, respectively. In the process of adjustment, the user himself or a person assisting in adjustment can easily arrange the acupoint stimulation mediums 31 located on the second bracket 13 and the moving parts 16 on the Shenting and the Fengchi at two sides by means of the positioning marks 18, wherein the Ermen, the Tinggong, the Tinghui, the Jiaosun and the Yifeng located around the ears are relatively dense, so that the corresponding acupoint stimulation mediums 31 are denser for each other. Therefore, the effectiveness of stimulation is not affected even if the acupoint stimulation mediums 31 located on the earmuffs do not accurately correspond to the Ermen, the Tinggong, the Tinghui, the Jiaosun and the Yifeng.

After the above steps are completed, the bent pipes 17 are adjusted so that the brain stimulation medium 41, which is an anode electrode, is moved and positioned to a position between C3 and T5 in a position of the international 10-20 system scalp electrode on the head of the user, and the brain stimulation medium 41, which is a cathode electrode, is moved and positioned to a position between T4 and F8. Finally, the electrode patches 51 of the transcutaneous electrical nerve stimulation device 5 are attached to the C2 nerve dermatome at the head and neck of the user (see FIG. 5), thus completing the wearing of the device. After the wearing is finished, the operation of the acupoint stimulation device 3, the brain stimulation device 4 and the transcutaneous electrical nerve stimulation device 5 can be simultaneously started and controlled by operating the control device 6, and the playing device 2 plays the music files so as to simultaneously carry out diversified hearing training.

In detail, the user may select the first frequency, i.e. the carrier frequency in each music file, to play the music file corresponding to the frequency of hearing loss according to his own frequency (the frequency that is less audible when performing a hearing test) of hearing loss. For example, in the frequency range (250-8000 Hz) where a sound is audible for a typical human ear at 40 dB, the 7000 Hz audio is not heard, namely 7000 Hz is the frequency of hearing loss of the user; and at the moment, the user can choose to play the music file with the first frequency, namely the carrier frequency, being 7000 Hz, and repeatedly play in decibels (up to 60 decibels) which can be heard by the user, and gradually reduce the decibels, thereby achieving the effect of hearing training. Due to the fact that the beat in each music file gradually decreases to 10-15 Hz with time, electroencephalogram of a user can be sequentially induced to enter a low-frequency range, and the processing area of auditory cortex are invigorated and regulated, so that the processing area of auditory cortex can be activated during the training, and a better training effect is achieved.

Figure 10:
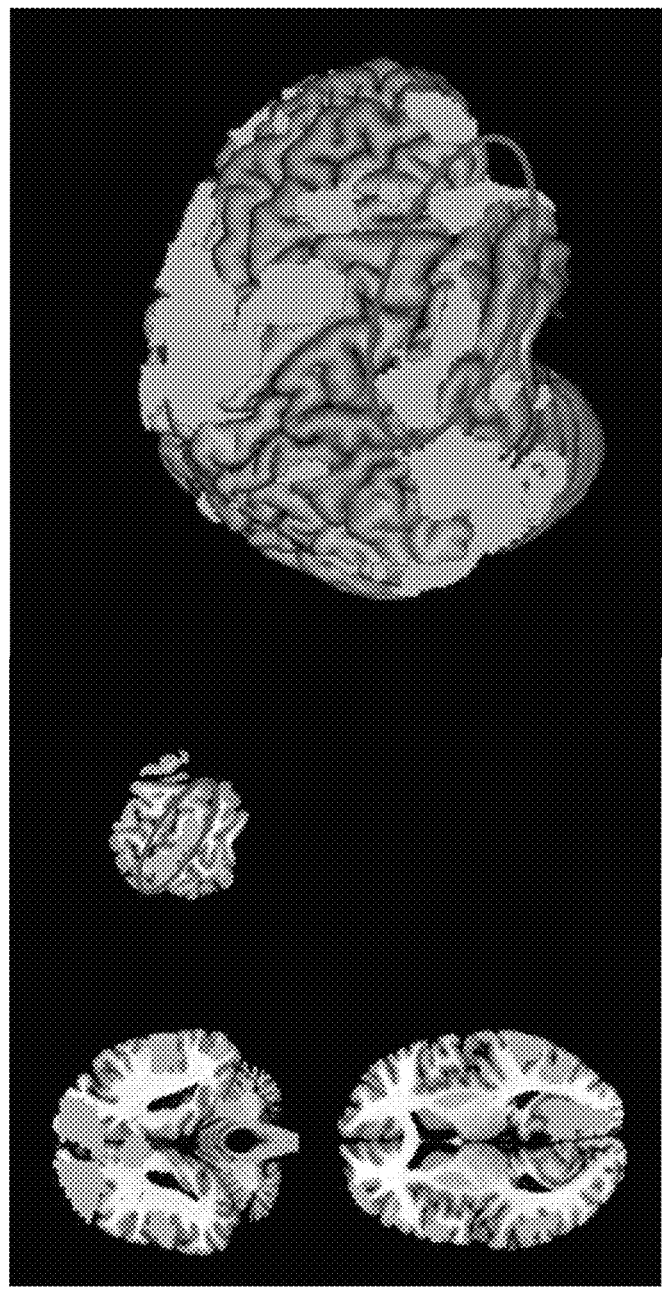
FIG. 10 is an analysis chart of a magnetic resonance image of one of subjects obtained after experimental analysis according to the present invention, illustrating a portion of the brain that is stimulated after the subject hears binaural beats music having a frequency difference between 10-15 Hz.
Figure 11:
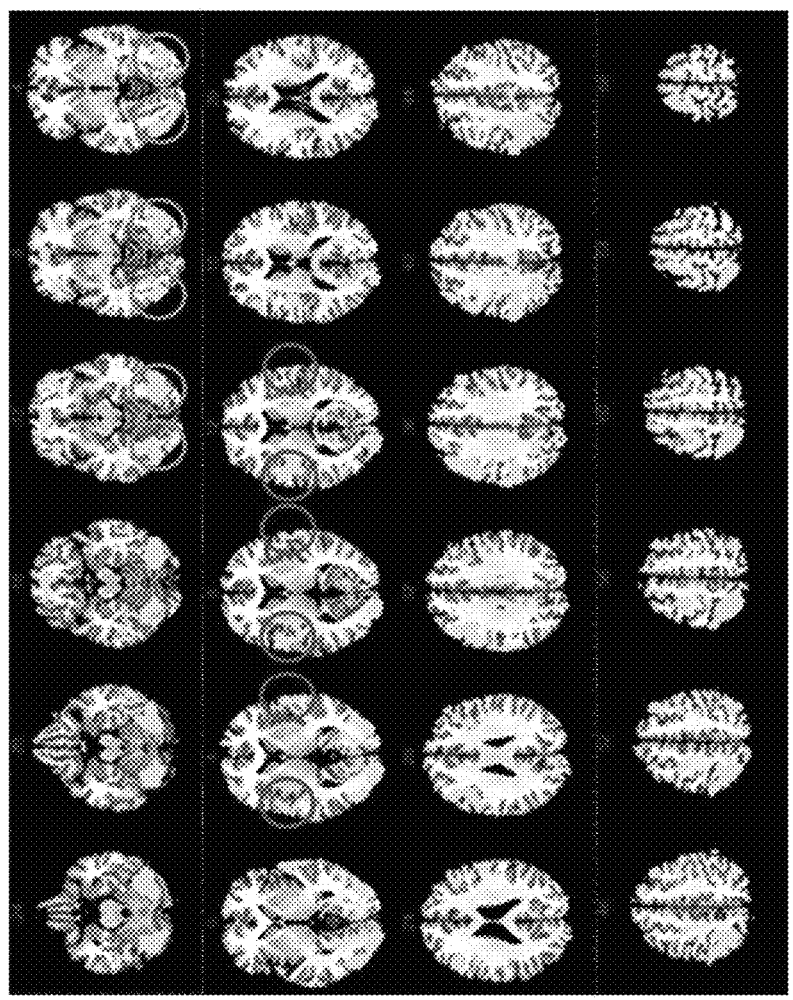
FIG. 11 is an analysis chart of a magnetic resonance image obtained by further analyzing the magnetic resonance image data of the subject of FIG. 10, illustrating the brain cortex that is stimulated after the subject hears binaural beats music having a frequency difference between 10-15 Hz.

Experiments prove that the beat in the music files gradually decreases to 10-15 Hz with time, the auditory cortex of a listener can be effectively stimulated, and the experimental steps are briefly described as follows: step 1, preparing a plurality of binaural beats music mixed with different beats; step 2, inviting a plurality of healthy subjects to listen to general music without binaural beats and monaural beats for 1 minute, collecting and analyzing neural activity in the brain by the magnetic resonance image, then inviting the subjects to listen to binaural beats music for 1 minute, and also collecting and analyzing neural activity in the brain by the magnetic resonance image; step 3, comparing the data of neural activity in the brain established by each subject after listening to the binaural beats music and the general music so as to establish the invigorated brain areas corresponding to the music with different beats. As can be from FIGS. 10 and 11, it shows the magnetic resonance image data obtained from a subject listening to binaural beats music at a beat between 10-15 Hz for 1 minute, and the portion encircled by the red circle is the location of the visual cortex and is seen to be significantly activated.

Figure 12:
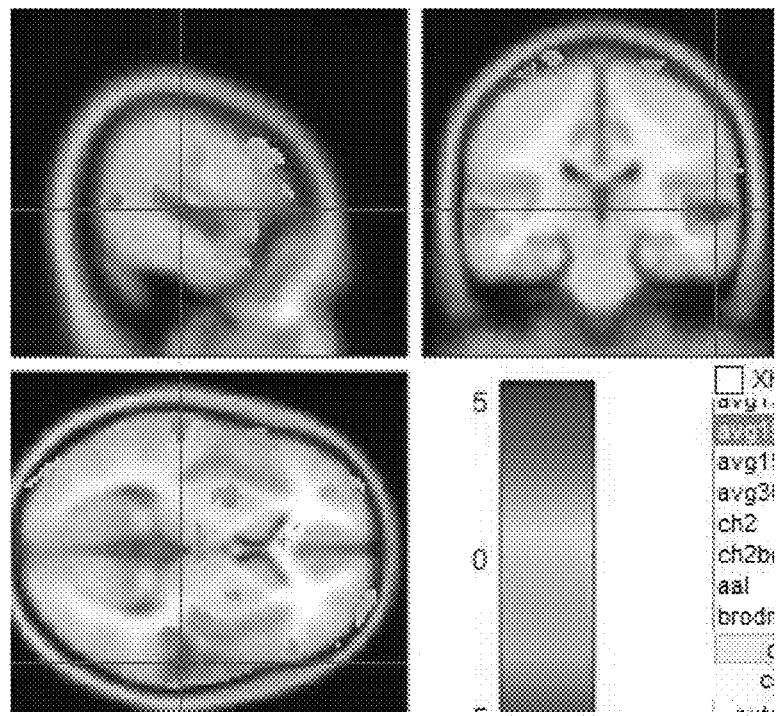
FIG. 12 is a magnetic resonance image data of another subject obtained after experimental analysis according to the present invention, illustrating the brain cortex that is stimulated after the subject hears binaural beats music having a frequency difference between 10-15 Hz.
Figure 13:
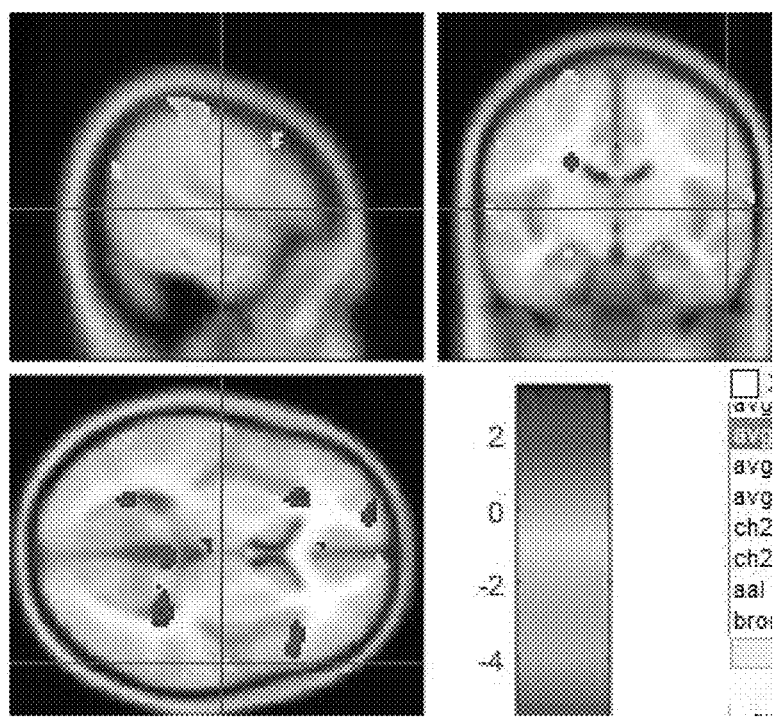
FIG. 13 is a magnetic resonance image data of yet another subject obtained after experimental analysis according to the present invention, illustrating the brain cortex that is stimulated after the subject hears binaural beats music having a frequency difference between 10-15 Hz.

FIGS. 12 and 13 show the magnetic resonance image data of two other subjects after listening to monaural beats music with a beat between 10-15 Hz for 1 minute. It can be seen from the cross-sectional images that in different subjects, the binaural beats music with a beat between 10-15 Hz produces a strong signal response to a posterior auditory cortex. It is known from research literature on the human auditory atlas (Mirror-Symmetric Tonotopic Maps in Human Primary Auditory Cortex, Elia, p 14, published by Formisano et al.) that the posterior auditory cortex mainly corresponds to the processing of high-frequency sounds, and this part is the brain cortex where a general person first degenerates and degrades the fastest. That is to say, the music files in the present invention can be widely applied to auxiliary training of general hearing-impaired users by mixing beats with frequencies between 10-15 Hz, and the method has a remarkable effect on invigorating the processing areas of auditory cortex.

Subjects:
(1) Experimental group: 2 subjects with high frequencies slopping sensorineural hearing loss; and
(2) Control group: 2 subjects with normal hearing.

FFR Treatment:

The whole FFR treatment contains two stages. Each stage requires a 3 days treatment.

At stage one, the participant requires to listen to 4 different frequencies tones for total 20 mins, with each frequency for 5 mins at their most comfortable level (MCL) each day for 3 days. All participants listened to 4 different tones depending on their hearing loss, one low frequency at their normal low frequency hearing range, 3 high frequencies at their hearing loss range.

After two weeks break, the second stage treatment was conducted by listening to 2 different frequencies tones (one low frequency and one high frequency at the hearing loss range) for 40 mins at MCL each day for 3 days.

Pure tone audiometry was conducted before and after each treatment for all participants. The results showed that both subjects with high frequencies slopping sensorineural hearing loss increased their high frequencies thresholds around 10-20 dB in average. For instance, at 10 kHz, one subject increased from 100 dB HL no response to 95 dB HL on the right ear, while the other subject increased from 100 dB HL to 80 dB HL on the left ear.

|            | 10K   | 11.2K | 12.5K | 14K  |
|------------|-------|-------|-------|------|
| RE (before)| 90    | 90    | 90    | 80NR |
| RE (after) | 80    | 85    | 85    | 80NR |
| LE (before)| 100   | 95NR  | 90NR  | 80NR |
| LE (after) | 80    | 85    | 85    | 70   |

|            | 10K   | 11.2K |
|------------|-------|-------|
| RE (before)| 100NR | 95NR  |
| RE (after) | 95    | 95    |
| LE (before)| 100NR | 95    |
| LE (after) | 100NR | 95    |

|            | 4K    |
|------------|-------|
| RE (before)| 15    |
| RE (after) | 0     |
| LE (before)| 15    |
| LE (after) | 0     |

|            | 8K    | 20K   |
|------------|-------|-------|
| RE (before)| 15    | 15NR  |
| RE (after) | 0     | 10    |
| LE (before)| 30    | 15NR  |
| LE (after) | 30    | 15    |

Conclusion:
1. Even no improvement observed on the day of the treatment, however, all subjects showed thresholds shift two weeks later.

2. Two subjects with presbycusis showed thresholds improvements at super high frequencies after two weeks treatment.

3. Two subjects with normal hearing (control group) also showed thresholds improvements at high frequencies after two weeks treatment.

In addition, the acupoint stimulation device 3 irradiates laser light on the acupoints P1-P8 to achieve the effect of imitating traditional acupuncture; and since the irradiated acupoints P1-P8 are all related to the hearing function, it can play an auxiliary training role aiming at the hearing function. The brain stimulation device 4 can be configured for stimulating the auditory area of the brain of a user with direct current between 0 and 2.5 mA so as to achieve an auxiliary hearing training effect, and the direct current output by the brain stimulation device 4 has the best auxiliary effect between 1.5-2 mA. By means of the transcutaneous electrical nerve stimulation device 5, a constant current with a pulse frequency of 1-200 Hz and an intensity of 0-100 mA can be output to a C2 nerve dermatome at the head and neck of the user, so that the auditory nerve can be regulated here, and the tinnitus phenomenon caused by the auditory nerve can be regulated.

In addition, the embodiment provides that when a user listens to the music files, acupoint stimulation and brain auditory cortex stimulation are carried out at the same time, so that a better training effect is achieved compared with only listening to a single audio frequency for hearing training, only performing acupoint stimulation and only performing brain auditory cortex stimulation.

Figure 15:
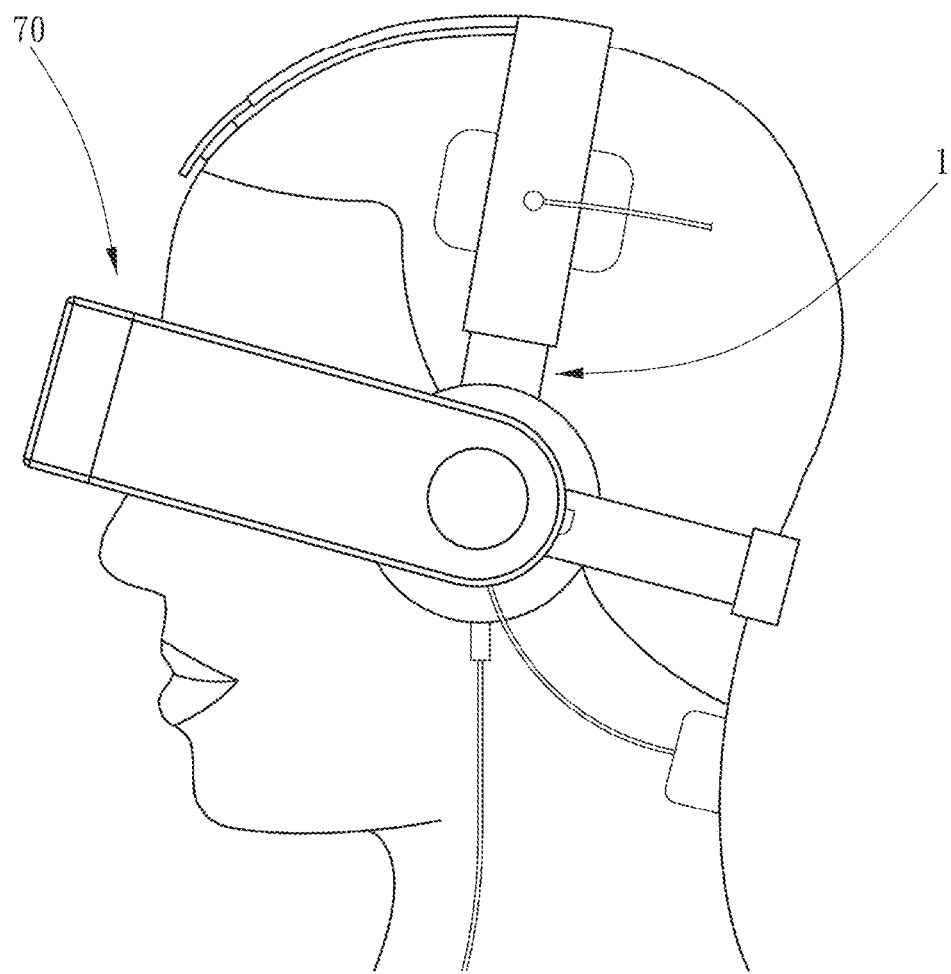
FIG. 15 is a schematic view of the hearing training device of the present invention equipped with a display and optical frequency stimulation unit.

Referring to FIG. 15, the hearing training device of the present invention may further comprise a display and optical frequency stimulation unit 70 arranged on the wearable device 1 and being switchable between a display mode and an optical frequency stimulation mode, wherein in the display mode, the display and optical frequency stimulation unit 70 displays a virtual image for the eyes of the user to view, so that the user can experience himself and receive education of hearing loss prevention; and in the optical frequency stimulation mode, the display and optical frequency stimulation unit 70 stimulate the eyes of the user in a flickering image, so that the activity of cranial nerves can be increased, brain network connectivity can be increased, the elimination of brain toxins can be promoted (Nature 540, 230-235, 2016), and the deterioration of hearing can be prevented.

To sum up, the advantages of this embodiment are summarized as follows.

1. The hearing training device can provide a new hearing training mode different from the previous one by virtue of the beat characteristics of the music files, and can be used for invigorating the brain auditory cortex of a user, particularly the auditory cortex corresponding to a high-frequency sound, namely the brain cortex where a general person first degenerates and degrades the fastest.

2. According to the embodiment, when a user listens to the music files, acupoint stimulation and brain auditory cortex stimulation are carried out at the same time, so that a better training effect is achieved compared with only listening to a single audio frequency for hearing training, only performing acupoint stimulation and only performing brain auditory cortex stimulation.

3. By means of the wearable device 1, a user can wear and position the playing device 2, the acupoint stimulation mediums 3, the brain stimulation mediums 4 and the electrode patches 5 on the head of the user at the same time, so that the acupoints, the brain auditory cortex and the auditory nerve behind the ears of the user can be stimulated at the same time. Compared with a physical rehabilitation device with a single general function, the embodiment can simultaneously carry out diversified auxiliary hearing training, and then the overall use time can be shortened.

4. By means of the structure of the wearable device 1, the acupoint stimulation mediums 3 can be quickly positioned at the positions of the acupoints P1-P8, and the acupoints P1-P8 are illuminated at the same time. According to the embodiment of the invention, the operation time (including acupoint selecting, positioning and illuminating time) of a professional can be greatly shortened, a user can use the wearable device 1 at home by himself even after the adjustment of the wearable device 1 is completed for the first time, and the use convenience is increased, compared with that only a single acupoint can be illuminated at one time by using a laser pen for general medical treatment, or traditional acupuncture requires the professional to locate each acupoint in sequence.

Figure 8:
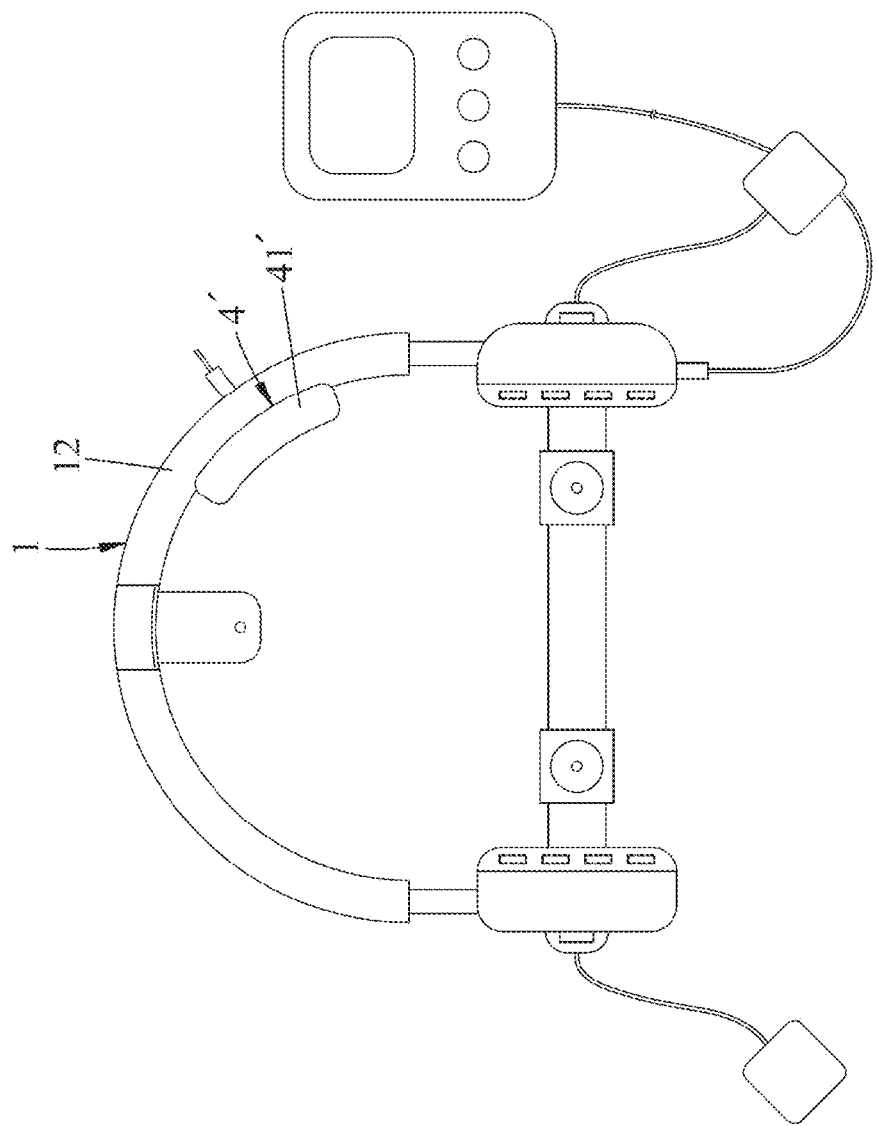
FIG. 8 is a schematically front view of a second embodiment of the hearing training device of the present invention.
Figure 9:
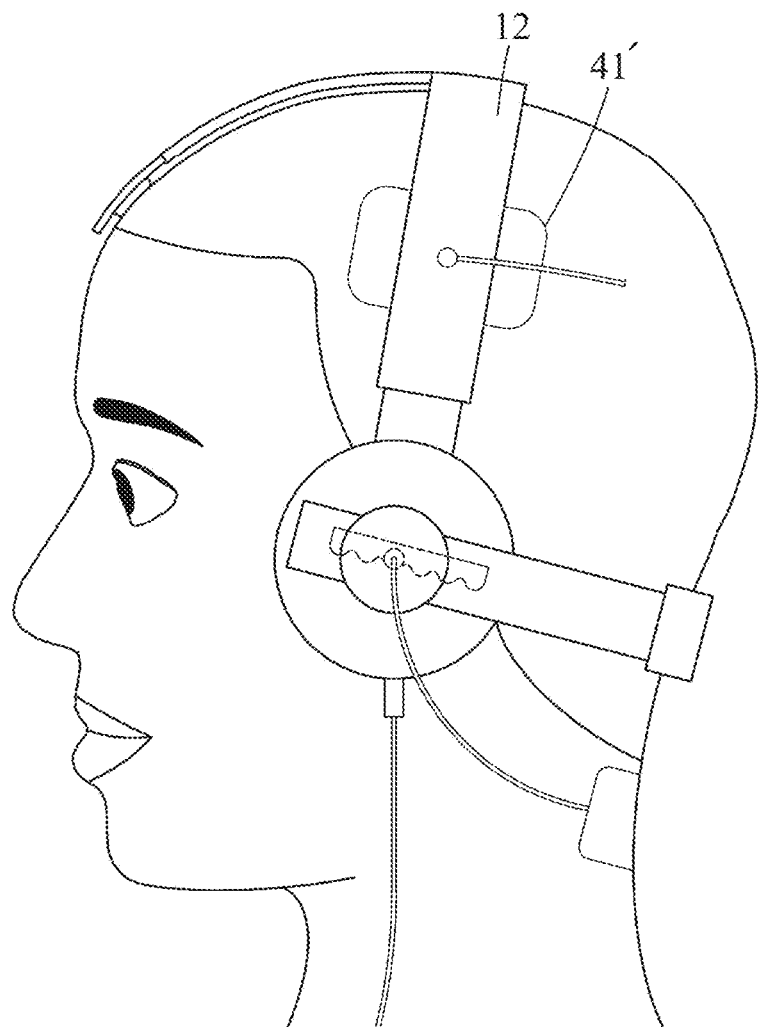
FIG. 9 is a fragmentary side view of the second embodiment illustrating a state in which the second embodiment is worn on the head of a user.

Referring to FIGS. 8 and 9, a second embodiment of the hearing training device of the present invention is similar to the first embodiment, with the difference in that the brain stimulation device 4' is a transcranial magnetic stimulation device, and comprises a brain stimulation medium 41' arranged on the first bracket 12, wherein the brain stimulation medium 41' is configured for corresponding to a position between C3 and T5 in a position of the international 10-20 system scalp electrode of the head of a user and can generate a magnetic field after being energized. Thereby, the brain stimulation device 4' can magnetically stimulate the user's brain by generating a magnetic field.

In summary, by means of the music files, the hearing training device can provide a new hearing training mode different from the prior art, can invigorate the auditory cortex of a user; and by means of the wearable device 1, the playing device 2, the acupoint stimulation mediums 31, the brain stimulation mediums 41 and the electrode patches 51 can be simultaneously worn and positioned on the head by the user to achieve the effect of simultaneously carrying out diversified auxiliary training and shorten the use time. Therefore, the purpose of the invention can be surely achieved.

The foregoing is only embodiments of the invention and shall not limit the scope of the invention. All simple equivalent changes and modifications made in accordance with the scope of the patent application for the invention and the contents of the patent description shall fall within the scope of the patent for invention.

Although particular embodiments of the invention have been described in detail for purposes of illustration, various modifications and enhancements may be made without departing from the spirit and scope of the invention. Accordingly, the invention is not to be limited except as by the appended claims.

What is claimed is:
1. A hearing training device, comprising:
a wearable device configured for being worn on the head of a user;
a playing device arranged on the wearable device;
an acupoint stimulation device, served as a physiotherapy device, comprising a plurality of acupoint stimulation mediums arranged on the wearable device, wherein each of the acupoint stimulation mediums is configured for stimulating one of a plurality of acupoints on the head of the user and related to hearing, and each of the acupoint stimulation mediums is arranged at one of the positions of the wearable device corresponding to one of the acupoints; and a control device being in signal connection with the playing device and storing at least one music file, wherein the control device controls the playing device to play the music file, a beat is formed in an audio track of the music file, the beat decreases with time, and the beat is fixed after the beat is between 10 Hz and 15 Hz; wherein the track of each music file is provided with a first audio frequency and a second audio frequency with a frequency difference therebetween, the first audio frequency and the second audio frequency form the beat, each music file is synthesized, the first audio frequency is a frequency of a carrier wave, the second audio frequency is a frequency of a modulated wave, the first audio frequency does not change with time, and the second audio frequency changes and approaches the first audio frequency with time so that the beat formed by the first audio frequency and the second audio frequency changes with time.

2. The hearing training device according to claim 1, wherein the control device stores a plurality of music files, and frequencies of the carrier waves of the music files range from 250-500±15 Hz, 500-750±15 Hz, 750-1000±15 Hz, 1000-1500±15 Hz, 1500-2000±15 Hz, 2000-3000±15 Hz, 3000-4000±15 Hz, 4000-6000±15 Hz, and 6000-8000±15 Hz respectively for a user to select a music file corresponding to his own frequency of hearing loss for playing; and the control device controls the playing device to play the music files with the sound intensity of 20-60 decibels, and the sound intensity can be adjusted between 20 and 60 decibels during playing.

3. The hearing training device according to claim 1, wherein the wearable device comprises two earmuffs for respectively covering both ears of a user, and a first bracket connected to the earmuffs and having an arc shape, wherein the first bracket is configured for straddling over the top of the head of the user, the acupoint stimulation mediums of the acupoint stimulation device are arranged on the earmuffs, and the corresponding acupoints are Tinghui, Ermen and Yifeng.

4. The hearing training device according to claim 3, wherein the first bracket of the wearable device has a central portion for corresponding to Baihui of the user, the wearable device further comprises a second bracket connected to the central portion and extending in a forward bending manner, and a third bracket connected to the earmuffs and having an arc shape; and the third bracket is configured for straddling over the hindbrain of the user, the acupoint stimulation mediums are arranged on the first bracket, the second bracket, the third bracket and the earmuffs, and the corresponding acupoints are Baihui, Shenting, Fengchi, Ermen, Tinggong, Tinghui, Jiaosun and Yifeng.

5. The hearing training device according to claim 4, wherein the second bracket of the wearable device has a front end positioned in front of the first bracket and provided with one of the acupoint stimulation mediums, and the front end can be approached backwards, moved forwards and away, and positioned relative to the central portion of the first bracket; the first bracket further has two connecting portions respectively connecting the earmuffs, each of the two connecting portions can be approached upwards, moved downwards and away, and positioned relative to the central portion of the first bracket; the third bracket is pivotally connected to the earmuffs, and can swing up and down and be positioned relative to the earmuffs; and the third bracket further comprises two moving parts arranged on the third bracket and spaced along an extending direction of the third bracket, and each moving part can move left and right and be positioned relative to the third bracket.

6. The hearing training device according to claim 5, wherein the third bracket of the wearable device comprises two pivoting portions pivotally connected to the earmuffs respectively, each pivoting portion has an elongated slot extending along the length direction thereof, and one side of the elongated slot is wavy; the wearable device further comprises two pivoting parts respectively connected to the elongated slot and connected with the earmuffs, the pivoting portions are rotatable about the pivoting parts, and the pivoting portions can be moved and positioned along the length direction thereof relative to the pivoting parts by the elongated slots; and the wearable device further comprises three positioning marks, wherein the positioning marks are respectively arranged on an outer side of the front end of the second bracket and an outer side of the moving parts, and the positions of the positioning marks correspond to the acupoint stimulation mediums arranged on the second bracket and the moving parts respectively, so that the user can distinguish the positions of the acupoint stimulation mediums from the outside.

7. The hearing training device according to claim 1, wherein the acupoint stimulation device is a laser device, the acupoint stimulation mediums are laser light generators and are configured for irradiating laser light to the acupoints, and the control device is in signal connection with the acupoint stimulation device and controls the operation of the acupoint stimulation device.

8. The hearing training device according to claim 1, further comprising a brain stimulation device in signal connection with and operated by the control device, wherein the brain stimulation device is a physiotherapy device and comprises at least one brain stimulation medium arranged on the wearable device, and the brain stimulation medium is configured for stimulating a brain cortex related to the hearing function of the user.

9. The hearing training device according to claim 8, wherein the brain stimulation device is a transcranial direct current stimulation device and comprises two brain stimulation mediums which are an anode electrode and a cathode electrode respectively and configured for outputting direct current between 0-2.5 mA; the wearing device further comprises two bent pipes which are respectively connected with the earmuffs and can be flexible and positioned, each bent pipe is provided with a moving end which is far away from the earmuff and respectively provided with the brain stimulation mediums; the moving ends of the bent pipes are movable and positioned to a position between C3 and T5 and a position between T4 and F8, respectively, in a position of an international 10-20 system scalp electrode of the user's head.

10. The hearing training device according to claim 1, further comprising a transcutaneous electrical nerve stimulation device in signal connection with and operated by the control device, wherein the transcutaneous electrical nerve stimulation device can perform transcutaneous electrical nerve stimulation, and comprises two electrode patches connected to the wearable device and configured for being attached to the C2 nerve dermatome at the head and neck of the user.

11. The hearing training device according to claim 1, further comprising a display and optical frequency stimulation unit arranged on the wearable device and being switchable between a display mode and an optical frequency stimulation mode, wherein in the display mode, the display and optical frequency stimulation unit displays a virtual image for the eyes of the user to view; and in the optical frequency stimulation mode, the display and optical frequency stimulation unit stimulates the eyes of the user with a flickering image.

\* \* \* \* \*